(12) United States Patent
Park et al.

(10) Patent No.: US 11,130,112 B2
(45) Date of Patent: Sep. 28, 2021

(54) FOULING PREVENTION METHOD AND METHOD FOR OLEFIN OLIGOMERIZATION

(71) Applicants: SK Innovation Co., Ltd., Seoul (KR); SK Global Chemical Co., Ltd., Seoul (KR)

(72) Inventors: Hyoseung Park, Daejeon (KR); Chansaem Park, Daejeon (KR); So Hee Sim, Daejeon (KR); Inhyoup Song, Daejeon (KR); Ilgu Jung, Daejeon (KR); Myungjin Kim, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 16/622,470

(22) PCT Filed: May 14, 2018

(86) PCT No.: PCT/KR2018/005477
§ 371 (c)(1),
(2) Date: Dec. 13, 2019

(87) PCT Pub. No.: WO2018/230844
PCT Pub. Date: Dec. 20, 2018

(65) Prior Publication Data
US 2020/0139333 A1      May 7, 2020

(30) Foreign Application Priority Data
Jun. 16, 2017   (KR) .................. 10-2017-0076529

(51) Int. Cl.
*B01J 19/00* (2006.01)
*C07C 2/34* (2006.01)
(Continued)

(52) U.S. Cl.
CPC ......... *B01J 19/002* (2013.01); *B01J 19/0026* (2013.01); *C07C 2/04* (2013.01);
(Continued)

(58) Field of Classification Search
CPC ............ B01J 19/002; B01J 2219/00247; B01J 19/0026; C07C 2/06; C07C 2/04;
(Continued)

(56) References Cited

U.S. PATENT DOCUMENTS 3,984,387 A   10/1976   Liu et al.
4,012,574 A   3/1977    Jones et al.
(Continued)

FOREIGN PATENT DOCUMENTS

EP   0237175 A1    9/1987
KR   101084937 B1  11/2011
(Continued)

*Primary Examiner* — Ali Z Fadhel
(74) *Attorney, Agent, or Firm* — The Webb Law Firm

(57) ABSTRACT

The present invention provides a fouling prevention method and a method for olefin oligomerization, wherein in the method for olefin oligomerization, a predetermined antifouling agent is added, thereby minimizing the production of sticking byproducts generated during the reaction and fundamentally preventing the fouling of the byproducts, generated during the reaction, on an inner wall of a reactor.

13 Claims, 1 Drawing Sheet

(51) Int. Cl.

| | |
|---|---|
| *C07C 7/20* | (2006.01) |
| *C10G 75/04* | (2006.01) |
| *C07C 2/06* | (2006.01) |
| *C07C 2/04* | (2006.01) |
| *C07C 2/36* | (2006.01) |
| *C07C 2/32* | (2006.01) |
| *C07C 2/08* | (2006.01) |
| *C07C 2/26* | (2006.01) |
| *C07C 11/107* | (2006.01) |
| *C07C 11/04* | (2006.01) |

(52) U.S. Cl.
CPC ............... *C07C 2/06* (2013.01); *C07C 2/08* (2013.01); *C07C 2/26* (2013.01); *C07C 2/32* (2013.01); *C07C 2/34* (2013.01); *C07C 2/36* (2013.01); *C07C 7/20* (2013.01); *C10G 75/04* (2013.01); *B01J 2219/00247* (2013.01); *C07C 11/04* (2013.01); *C07C 11/107* (2013.01)

(58) Field of Classification Search
CPC .... C07C 2/36; C07C 2/32; C07C 2/08; C07C 2/26; C07C 2/34; C07C 7/20; C07C 11/04; C07C 11/107; C07C 11/06; C10G 75/04; Y02P 20/52
See application file for complete search history.

(56) References Cited

U.S. PATENT DOCUMENTS

| | | | |
|---|---|---|---|
| 4,024,051 A * | 5/1977 | Shell ................. | C10G 7/10 |
| | | | 208/348 |
| 4,675,463 A | 6/1987 | Glivicky et al. | |
| 4,956,427 A | 9/1990 | Jenkins, III et al. | |
| 8,445,609 B2 | 5/2013 | Tohi et al. | |
| 9,359,455 B2 | 6/2016 | Morrison et al. | |
| 10,413,893 B2 | 9/2019 | Shin et al. | |
| 2007/0142220 A1 | 6/2007 | Ok et al. | |
| 2008/0293860 A1* | 11/2008 | De Munck ............ | C07C 7/20 |
| | | | 524/323 |
| 2012/0016079 A1 | 1/2012 | Weber et al. | |
| 2016/0367977 A1 | 12/2016 | Shaikh et al. | |
| 2017/0305811 A1* | 10/2017 | Shin ................... | C08K 5/00 |
| 2018/0142047 A1 | 5/2018 | Jensen et al. | |
| 2018/0327332 A1* | 11/2018 | Sogo ................... | C07C 2/32 |

FOREIGN PATENT DOCUMENTS

| | | |
|---|---|---|
| KR | 101327598 B1 | 11/2013 |
| KR | 101588382 B1 | 1/2016 |
| KR | 1020160099449 A | 8/2016 |
| WO | 2016183006 A1 | 11/2016 |
| WO | 2016205194 A1 | 12/2016 |

* cited by examiner

【FIG. 1】
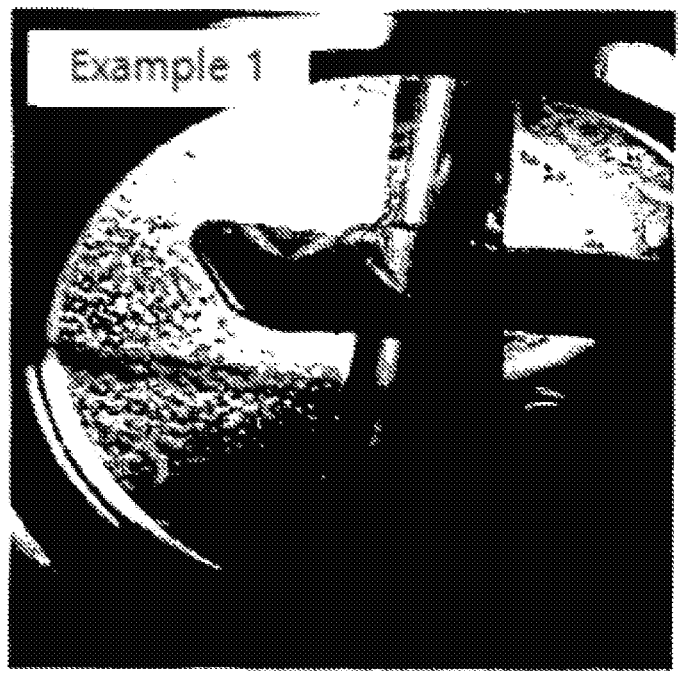
【FIG. 2】
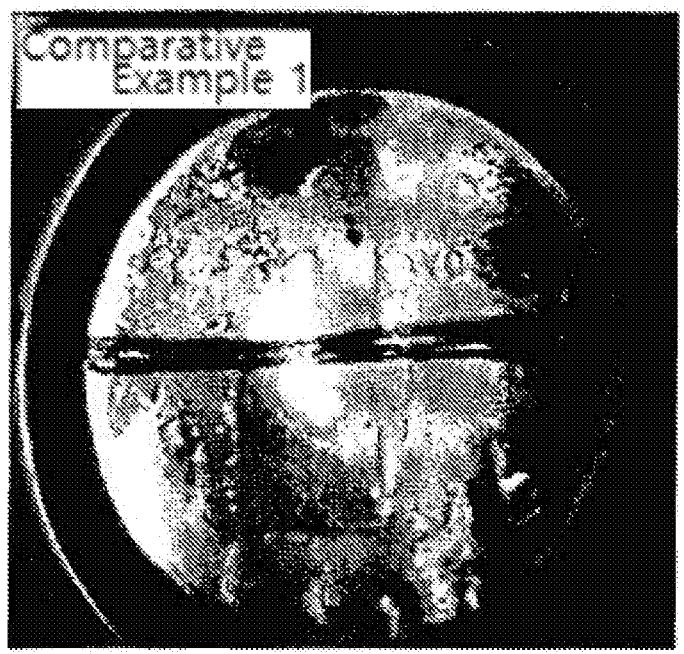

FOULING PREVENTION METHOD AND METHOD FOR OLEFIN OLIGOMERIZATION

CROSS-REFERENCE TO RELATED APPLICATIONS

This application is the United States national phase of International Application No. PCT/KR2018/005477 filed May 14, 2018, and claims priority to Korean Patent Application No. 10-2017-0076529 filed Jun. 16, 2017, the disclosures of which are hereby incorporated by reference in their entirety.

TECHNICAL FIELD

The present invention relates to an antifouling method and an olefin oligomerization method.

BACKGROUND ART

A linear α-olefin (LAO) required for preparation of a high value-added linear low density polyethylene is obtained by an oligomerization reaction of an olefin. However, the oligomerization reaction of an olefin produces significant amounts of butene, other olefins, and isomers thereof, specific higher oligomers, polymers (for example, polyethylene), and the like together, and a catalyst released from a carrier and by-products (for example, polyethylene) produced during an oligomerization reaction of an olefin are partly attached to the inner wall of a reactor and on the surface of a heat exchanger installed in the reactor or float in the reactor to form fouling.

Fouling as described above makes it difficult to control a heat of reaction and interfere with even diffusion of an olefin monomer to reduce heat efficiency and production efficiency.

Thus, various embodiments of technologies for suppressing fouling in the reactor as described above have been suggested. First, U.S. Pat. No. 4,956,427 discloses a method of hydrolyzing and curing aminosilicon on a metal surface in a reactor to coat it. However, the method has a problem in that a high cost is required since, for example, during coating, production should be stopped for a long time. Next, U.S. Pat. No. 3,984,387 discloses a method of introducing inert gas such as nitrogen and helium to a reactor together with an olefin monomer, but has a problem that a partial pressure of the olefin monomer is decreased to degrade a polymerization activity. Next, U.S. Pat. No. 4,012,574 discloses method of introducing an antifouling agent including a perfluorocarbon group and a hydrophilic group, but has a problem that an effect of suppressing fouling is not sufficient.

Thus, the present inventors confirmed that in an olefin oligomerization method, process problems such as fouling and plugging may be effectively solved to provide improved workability and productivity, thereby completing the present invention.

DISCLOSURE

Technical Problem

An object of the present invention is to provide an ionic compound useful as an antifouling agent.

Another object of the present invention is to provide a reactor antifouling method which not only has a significant effect of decreasing fouling occurring during the reaction, but also does not cause an adverse effect to reaction efficiency, using an ionic compound.

Still another object of the present invention is to provide an olefin oligomerization method which suppresses production of by-products (for example, polyethylene) occurring during an olefin oligomerization reaction and effectively suppresses sticking of the produced by-products in a reactor simultaneously, thereby showing an excellent effect of decreasing fouling.

In particular, the olefin oligomerization method according to the present invention allows easy removal of a heat of reaction by the above-described effect, may maximize a catalyst activity, and may produce 1-hexene and 1-octene with high selectivity by oligomerization.

Technical Solution

In one general aspect, a reactor antifouling method includes introducing an antifouling agent including an ionic compound to a chemical reactor.

In the reactor antifouling method according to an exemplary embodiment of the present invention, the ionic compound having various forms selected from the group consisting of inorganic salts and organic salts may be used as the antifouling agent.

In the reactor antifouling method according to an exemplary embodiment of the present invention, the inorganic salt may be selected from the group consisting of alkali metal salts, alkali earth metal salts, transition metal salts, post-transition metal salts, metalloid salts, and the like.

In the reactor antifouling method according to an exemplary embodiment of the present invention, cations of the organic salts may be selected from the group consisting of ammonium, phosphonium, pyridinium, imidazolium, imidazolinium, pyrazolium, sulfonium, pyrrolidinium, piperidinium, and the like.

In the reactor antifouling method according to an exemplary embodiment of the present invention, the ionic compound may be included in a range of 0.001 to 1,000 ppm, based on a total weight of the medium.

In another general aspect, an olefin oligomerization method includes: introducing an antifouling agent including an ionic compound to a medium introduced into a reactor; introducing a catalyst composition to the reactor; and introducing an olefin to the reactor to subject the olefin to an oligomerization reaction.

In the olefin oligomerization method according to an exemplary embodiment of the present invention, the ionic compound may be an inorganic salt including a metal ion selected from the group consisting of alkali metals, alkali earth metals, transition metals, post-transition metals, metalloids, and the like.

In the olefin oligomerization method according to an exemplary embodiment of the present invention, the ionic compound may be selected from the group consisting of alkali metal salts and the like.

In the olefin oligomerization method according to an exemplary embodiment of the present invention, the ionic compound may be selected from organic salts including cations selected from the group consisting of ammonium, phosphonium, pyridinium, imidazolium, pyrazolium, sulfonium, pyrrolidinium, piperidinium, and the like.

In the olefin oligomerization method according to an exemplary embodiment of the present invention, the ionic compound may be selected from the group consisting of tetraalkyl ammonium salts, tetraalkyl phosphonium salts, and the like.

In the olefin oligomerization method according to an exemplary embodiment of the present invention, the ionic compound may be selected from tetraalkyl ammonium salts selected from the group consisting of tetraalkyl ammonium phosphate-based compounds, tetraalkyl ammonium sulfate-based compound, tetraalkyl ammonium halide-based compound, tetraalkyl ammonium pseudohalide-based compounds, and the like; tetraalkyl phosphonium salts selected from the group consisting of tetraalkyl phosphonium phosphate-based compounds, tetraalkyl phosphonium sulfate-based compound, tetraalkyl phosphonium halide-based compound, tetraalkyl phosphonium pseudohalide-based compounds, and the like; and the like.

In the olefin oligomerization method according to an exemplary embodiment of the present invention, the ionic compound may include a halide group.

In the olefin oligomerization method according to an exemplary embodiment of the present invention, the ionic compound may be included in a range of 0.001 to 1,000 ppm, based on a total weight of the medium.

In the olefin oligomerization method according to an exemplary embodiment of the present invention, the catalyst composition includes a main catalyst and a cocatalyst, and the main catalyst may be a complex of a transition metal coordinately bonded to a heteroatom ligand represented by the following Chemical Formula A:

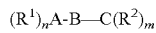

[Chemical Formula A]

wherein

A and C are independently of each other selected from the group consisting of phosphorus, arsenic, antimony, oxygen, bismuth, sulfur, selenium, and nitrogen, B is a linking group between A and C, n and m are independently of each other an integer determined by each of valency and oxidation state of A or C, $R^1$ and $R^2$ are independently of each other selected from the group consisting of substituted or unsubstituted hydrocarbyl and substituted or unsubstituted heterohydrocarbyl, and when n≥2, $R^1$'s may be identical to or different from each other, and when m≥2, $R^2$'s may be identical to or different from each other.

In the olefin oligomerization method according to an exemplary embodiment of the present invention, a reaction step may be performed in a temperature range of 0 to 200° C.

In the olefin oligomerization method according to an exemplary embodiment of the present invention, the reaction step may be performed in a temperature range of 40 to 100° C.

In the olefin oligomerization method according to an exemplary embodiment of the present invention, the reaction step may be performed in a pressure range of 1 to 800 bar.

The olefin oligomerization method according to an exemplary embodiment of the present invention may be selectively preparing 1-hexene, 1-octene, or a mixture thereof.

Advantageous Effects

According to the present invention, the production amount of sticking by-products is effectively suppressed, and also the production amounts of floating by-products as well as the sticking by-products are dramatically suppressed by using a predetermined ionic compound, thereby fundamentally preventing fouling of the by-products produced during the reaction in the inner wall of a reactor. Thus, since thermal conductivity in the inner wall of the reactor may be maintained constant, temperature control during the reaction becomes easy and reaction efficiency may be maximized.

According to the present invention, due to an effectively controlled effect of decreasing fouling, rapid initiation, stable operation, and good reproducibility of an olefin oligomerization reaction may be realized with maximized reaction efficiency.

Moreover, according to the present invention, since in the by-products produced during the reaction, the production amount of sticking by-products which are stuck in the inner wall of the reactor, may be suppressed to a minimum amount, and also a technical obstructive factor of the conventional art is overcome and a synergistic effect in a decreased production amount of the by-products which are produced during the reaction may be achieved, a production efficiency increase effect may be provided.

DESCRIPTION OF DRAWINGS

FIG. 1 is an image of an inside of a reactor after a reaction of Example 1 according to the present invention.

FIG. 2 is an image of an inside of a reactor after a reaction of Comparative Example 1 according to the present invention.

BEST MODE

Hereinafter, the antifouling method and the olefin oligomerization method according to the present invention will be described, however, technical terms and scientific terms used herein have the general meaning understood by those skilled in the art to which the present invention pertains unless otherwise defined, and a description for the known function and configuration obscuring the present invention will be omitted in the following description.

The term, "ionic compound" herein includes not only an optional polar liquid simply including ions, but also all polar compounds which have a vapor pressure close to 0 and is polar in a temperature range of −100 to 300° C. In addition, the polarity may vary with the kind of anionic materials, and various kinds of ionic compounds having from a very weak polarity to a very strong polarity may be used as an exemplary embodiment of the present invention.

The term, "fouling" herein refers to a continuous work problem by a by-product produced during a reaction which is discontinuously caused in a reactor, and the fouling may be present in at least two different forms. The two forms of fouling are described as sticking fouling or floating fouling depending on at which position of the reactor the produced by-product is formed. In addition, the sticking by-product is expressed as a sticking polymer, a secondary polymer, sticking polyethylene, $2^{nd}$ PE, and the like, which are the terms of the present invention, and the floating fouling may be expressed as a floating polymer, a primary polymer, floating polyethylene, $1^{st}$ PE, and the like, which are the terms of the present invention.

The term of the present invention, "oligomerization" means that the olefin is oligomerized. Oligomerization is referred to as trimerization or tetramerization depending on the number of olefins to be polymerized, and these are collectively called multimerization. In particular, in the present specification, oligomerization means that ethylene is trimerized and tetramerized to selectively produce 1-hexene and 1-octene which are the main comonomers of linear low-density polyethylene.

The antifouling agent according to an exemplary embodiment of the present invention has a significant fouling reduction effect. In particular, the above-described effect becomes significant by suppressing the production amount of a sticking floating matter which is stuck to the inner wall of a reactor to a minimum.

In addition, the antifouling agent according to an exemplary embodiment of the present invention does not affect the physical properties and the catalytic efficiency of a linear α-olefin (for example, 1-hexene, 1-octene, and the like) which is produced by the oligomerization reaction described above, and has an excellent fouling reduction effect in spite of a small use amount.

The antifouling agent according to an exemplary embodiment of the present invention includes an ionic compound.

The ionic compound which may be included in the antifouling agent according to an exemplary embodiment of the present invention means that the compound includes a cationic component with an anionic component, and each of the components may have a significant influence on the solubility of the ionic compound in different media.

According to an exemplary embodiment of the present invention, the anionic component of the ionic compound may be a polyvalent anionic component which is a monovalent, divalent, or higher-valent. The anionic component is not limited, but a non-limiting example of the anionic component may include that having one or more anionic groups selected from the group consisting of alkoxide groups or aryloxide groups such as $RO^-$ (wherein R is alkyl or aryl); halide groups such as $F^-$, $Cl^-$, $Br^-$, and $I^-$; pseudohalide groups such as $BF_4^-$, $PF_6^-$, $CF_3SO_3^-$, $(CF_3SO_3)_2N^-$, $CN^-$, $SCN^-$, and $OCN^-$; sulfonate groups or sulfate group such as $CF_3SO_3^-$, $CH_3(C_6H_4)SO_3^-$, $CH_3C_6H_4SO_3^-$, $COOH(C_6H_4)SO_3^-$, $CF_3SO_3^-$, and $SO_4^{2-}$; carbonate groups or carboxylate groups such as $CO_3^{2-}$, $C_6H_5COO^-$, $CH_3COO^-$, and $CF_3COO^-$; borate groups such as $B_4O_7^{2-}$, $BF_4^-$, and $B(C_6H_5)_4^-$; arsenate groups such as $AsF_6^-$; phosphate groups; nitrite groups or nitrate groups; and the like.

The ionic compound included in the antifouling agent according to an exemplary embodiment of the present invention may be one or more selected from the group consisting of inorganic salts, organic salts, and the like.

The inorganic salt included the antifouling method according to an exemplary embodiment of the present invention may be that including a metal ion selected from the group consisting of alkali metals, alkali earth metals, transition metals, post-transition metals, metalloids, and the like, as a cationic component. Here, examples of the metal ion may include alkali metals such as Li, Na, K, and Cs; alkali earth metals such as Be, Ca, and Mg; transition metals such as Au, Ag, Fe, Cu, Ni, and Co; post-transition metals such as Al, Ga, and In; metalloids such as B, Si, Ge, and As; and the like, but are not limited thereto.

A non-limiting example of the inorganic salt included in the antifouling agent according to an exemplary embodiment of the present invention may be one or more selected from the group consisting of NaCl, NaBr, NaF, NaI, KCl, KBr, KF, KI, $Na_2S$, $K_2S$, $NaHCO_3$, $Na_2CO_3$, $NaHSO_3$, $Na_3PO_4$, $Na_2HPO_4$, $KHCO_3$, $K_2CO_3$, $KHSO_3$, $K_3PO_4$, $K_2HPO_4$, and the like. In particular, the inorganic salt included in the antifouling agent according to an exemplary embodiment of the present invention may be an alkali metal salt, in terms of optimally reducing the sticking by-product, and a non-limiting example thereof may include NaCl, NaBr, NaF, NaI, KCl, KBr, KF, KI, $Na_3PO_4$, $Na_2HPO_4$, $K_3PO_4$, $K_2HPO_4$, and the like.

The organic salt included in the antifouling method according to an exemplary embodiment of the present invention may include a cationic component selected from the group consisting of ammonium, phosphonium, pyridinium, imidazolium, imidazolinium, pyrazolium, sulfonium, pyrrolidinium, piperidinium, and the like.

A non-limiting example of the organic salt included in the antifouling agent according to an exemplary embodiment of the present invention may include ionic compounds including a cationic component selected from the group consisting of ammonium such as N-ethyl-N,N-dimethyl-N-propylammonium, N,N,N-trimethyl-N-propylammonium, N-methyl-N,N,N-tributylammonium, N-ethyl-N,N,N-tributylammonium, N-methyl-N,N,N-trihexylammonium, N-ethyl-N,N,N-trihexylammonium, N-methyl-N,N,N-trioctylammonium, or N-ethyl-N,N,N-trioctylammonium; phosphonium such as N-ethyl-N,N-dimethyl-N-propylphosphonium, N,N,N-trimethyl-N-propylphosphonium, N-methyl-N,N,N-tributylphosphonium, N-ethyl-N,N,N-triphosphoammonium, N-methyl-N,N,N-trihexylphosphonium, N-ethyl-N,N,N-trihexylphosphonium, N-methyl-N,N,N-trioctylphosphonium, or N-ethyl-N,N,N-trioctylphosphonium; pyridinium such as tetrahydropyridinium or dihydropyridinium; imidazolium; imidazolinium such as 1-ethyl-3-methylimidazolinium; pyrazolium; sulfonium; pyrrolidinium such as 1-methyl-1-propyl pyrrolidinium; piperidinium such as methyl-1-propyl piperidinium; and the like, and a anionic component described above.

When the antifouling agent according to an exemplary embodiment of the present invention includes, particularly, a predetermined ionic compound including a cationic component selected from the group consisting of tetraalkylammonium and tetraalkkylphosphonium, the production amounts of floating by-products as well as sticking by-products may be dramatically suppressed.

That is, when the predetermined ionic compound described above is used as the antifouling agent, the total amounts of the by-products produced during the reaction are minimized, and also a phenomenon of fouling in the inner wall of the reactor resulted therefrom may be fundamentally prevented.

Preferably, the predetermined ionic compound may be one or more selected from the group consisting of tetraalkylammonium phosphate-based compounds, tetraalkylammonium sulfate-based compounds, tetraalkylammonium halide-based compounds, tetraalkylammonium pseudohalide-based compounds, tetraalkylphosphonium phosphate-based compounds, tetraalkylphosphonium sulfate-based compounds, tetraalkylphosphonium halide-based compounds, tetraalkylphosphonium pseudohalide-based compounds, and the like.

The alkyl in the ionic compound may be in the form of a straight chain or branched chain form having 1 to 50 carbon atoms, and preferably, has one or more lower alkyl having 1 to 7 carbon atoms, in terms of effectively changing an occurrence behavior of the produced by-products. However, a higher alkyl having 8 or more carbon atoms is also an exemplary embodiment of the present invention.

In addition, the ionic compound may include the anionic component selected from the group consisting of halide groups such as $F^-$, $Cl^-$, $Br^-$, and $I^-$; pseudohalide groups such as $BF_4^-$, $PF_6^-$, $CF_3SO_3^-$, $(CF_3SO_3)_2N^-$, $CN^-$, $SCN^-$, and $OCN^-$; sulfate groups represented by the following Chemical Formula 1; ad phosphate groups represented by the following Chemical Formula 2:

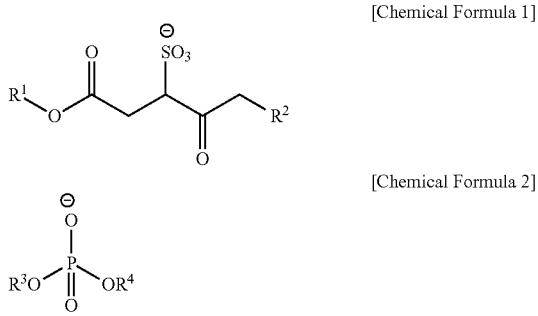

[Chemical Formula 1]

[Chemical Formula 2]

wherein $R^1$ to $R^4$ are independently of one another selected from the group consisting of hydrogen, substituted or unsubstituted hydrocarbyl, and substituted or unsubstituted heterohydrocarbyl, and $R^3$ and $R^4$ are not hydrogen at the same time.

In the anionic component represented by Chemical Formulae 1 and 2, it is preferred that $R^1$ to $R^4$ are independently of one another selected from the group consisting of hydrogen, (C6-C20)aryl, (C6-C20)ar(C1-C10)alkyl, (C1-C10)alkyl, (C1-C10)alkoxycarbonyl(C1-C10)alkyl, carbonyl(C1-C10)alkyl, (C2-C10)alkenyl, (C2-C10)alkynyl, (C3-C7)cycloalkyl, (C5-C20)heteroaryl, (C3-C7)heterocycloalkyl, (C1-C10)alkoxy, (C6-C20)aryloxy, and the like, and $R^3$ and $R^4$ may not be hydrogen at the same time.

In addition, the ionic compound included in the antifouling agent according to an exemplary embodiment of the present invention may include a halide group.

Hereinafter, the antifouling method using the antifouling agent according to an exemplary embodiment of the present invention will be described. The antifouling agent may be used in an olefin oligomerization process.

The antifouling method according to an exemplary embodiment of the present invention includes introducing an ionic compound.

Here, the condition of introducing the ionic compound in the above method is not limited, and for example, the ionic compound may be preliminary introduced to a cocatalyst and a main catalyst for olefin oligomerization, may be introduced during introduction of the cocatalyst and the main catalyst, or may be further added after completing addition of the cocatalyst and the main catalyst.

In the antifouling method according to an exemplary embodiment of the present invention, the use amount of the ionic compound is not limited, but the ionic compound may be used by appropriately adjusting the amount to 0.001 to 1,000 ppm, 0.01 to 500 ppm, 0.1 to 50 ppm, or 10 to 30 ppm in a medium used in the reaction.

According to an exemplary embodiment of the present invention, the ionic compound is served as a lubricant during the reaction to effectively suppress sticking of the by-products produced during the reaction to the inner wall of the reactor, and to change the occurrence behavior of the polymer produced as the by-product during the reaction to minimize the total production amount of the polymer.

Thus, the thermal conductivity in the inner wall of the reactor may be maintained constant, which allows easy control of the heat of reaction and is helpful to even diffusion of an olefin and catalytic activity, thereby providing improved production efficiency.

Specifically, as the antifouling method using the antifouling agent according to an exemplary embodiment of the present invention, an olefin oligomerization method with reduced fouling will be described.

According to an exemplary embodiment of the present invention, in the by-products produced during olefin oligomerization, the production amount of sticking by-products stuck in the reactor may be suppressed to a minimum. In addition, by adopting the predetermined ionic compound according to the present invention, the production amounts of the floating by-products as well as the sticking by-products are effectively suppressed, thereby problems in the process occurring by the by-products may be dramatically prevented.

Thus, according to an exemplary embodiment of the present invention, the problems in the process, such as fouling or plugging in the reactor, occurring during olefin oligomerization are solved to provide improved workability and productivity. Moreover, by effectively suppressing the problems in the process such as fouling or plugging in the reactor, degradation of the catalytic activity which may be caused during the reaction may be prevented. Here, the by-products produced during the reaction in particular, the sticking by-products, are stuck in the reactor and interfere with heat transfer to decrease a LAO production yield, and serves to induce prevention of operation of the process.

In addition, according to an exemplary embodiment of the present invention, in particular, ethylene is trimerized and tetramerized with improved catalytic activity to produce 1-hexene and 1-octene with high selectivity.

The olefin oligomerization method with reduced fouling according to an exemplary embodiment of the present invention includes: introducing an antifouling agent including an ionic compound to a medium introduced into a reactor, introducing a catalyst composition to the reactor, and introducing an olefin to the reactor to subject the olefin to an oligomerization reaction. Here, the ionic compound may be one or more selected from the group consisting of inorganic salts and organic salts.

In the olefin oligomerization method with reduced fouling according to the present invention, the ionic compound may be selected from inorganic salts including a metal ion selected from the group consisting of alkali metals, alkali earth metals, transition metals, post-transition metals, metalloids, and the like; organic salts including a cationic component selected from the group consisting of ammonium, phosphonium, pyridinium, imidazolium, imidazolinium, pyrazolium, sulfonium, pyrrolidinium, piperidinium, and the like; and the like.

In the olefin oligomerization method with reduced fouling according to an exemplary embodiment of the present invention, when one or more ionic compounds selected from the inorganic salts are used, not only does no disadvantage result in the production amount of LAO, but also the production amount of the sticking by-products may be dramatically suppressed.

In addition, in the olefin oligomerization with reduced fouling according to an exemplary embodiment of the present invention, when one or more ionic compounds selected from the organic salts are used, the production amount of the floating by-products as well as the production amount of the sticking by-products are minimized, thereby significantly decreasing the phenomenon of fouling in the inner wall of the reactor.

Preferably, in the olefin oligomerization method with reduced fouling according to an exemplary embodiment of the present invention, it is preferred to include one or more ionic compounds selected from the group consisting of tetraalkylammonium phosphate-based compounds, tetraalkylammonium sulfate-based compounds, tetraalkylammonium halide-based compounds, tetraalkylammonium pseudohalide-based compounds, tetraalkylphosphonium phosphate-based compounds, tetraalkylphosphonium sulfate-based compounds, tetraalkylphosphonium halide-based compounds, tetraalkylphosphonium pseudohalide-based compounds, and the like, as the organic salt.

More preferably, in the olefin oligomerization method with reduced fouling according to an exemplary embodiment of the present invention, it is preferred to include one or more organic salts selected from the group consisting of tetramethylammonium bromide, tetramethylammonium chloride, tetramethylammonium fluoride, tetramethylammonium cyanide, tetraethylammonium bromide, tetraethylammonium chloride, tetraethylammonium fluoride, tetraethylammonium cyanide, tetrabutylammonium bromide, tetrabutylammonium chloride, tetrabutylammonium fluoride, tetrabutylammonium cyanide, and the like, as the ionic compound, since the fouling effect to be desired is shown to be significant.

In the olefin oligomerization method with reduced fouling according to an exemplary embodiment of the present invention, the ionic compound may include a halide group.

In addition, when the predetermined ionic compound described above is included, the total production amount of the by-products produced during the reaction is reduced to effectively suppress fouling in the reactor and dramatically improve reaction efficiency simultaneously, thereby imparting high selectivity to oligomerization of an olefin, in particular, trimerization and tetramerization of ethylene.

Here, the introduction order of the ionic compound and the catalyst composition has no influence on the reaction, and the introduction order may be appropriately adjusted according to convenience in the process.

In the olefin oligomerization method with reduced fouling according to an exemplary embodiment of the present invention, the use amount of the ionic compound is not limited, but the ionic compound may be used by appropriately adjusting the amount to 0.001 to 1,000 ppm, 0.01 to 500 ppm, 0.1 to 50 ppm, or 10 to 30 ppm in a medium of the olefin oligomerization process.

In the olefin oligomerization method with reduced fouling according to an exemplary embodiment of the present invention, the catalyst composition includes a main catalyst and a cocatalyst, and the main catalyst is not limited as long as it is in the form of a complex which may oligomerize an olefin, but preferably the main catalyst includes a transition metal, and may be a catalyst in which a heteroatom ligand is coordinately bonded.

Preferably, the main catalyst according to the present invention may be in the form of a complex in which a transition metal and a heteroatom ligand are coordinately bonded, represented by the following Chemical Formula 1:

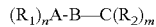  [Chemical Formula A]

wherein

A and C are independently of each other selected from the group consisting of phosphorus, arsenic, antimony, oxygen, bismuth, sulfur, selenium, and nitrogen, B is a linking group between A and C, n and m are independently of each other an integer determined by each of valency and oxidation state of A or C, and $R^1$ and $R^2$ are independently of each other selected from the group consisting of substituted or unsubstituted hydrocarbyl and substituted or unsubstituted heterohydrocarbyl, and when n≥2, $R^1$'s may be identical to or different from each other, and when m≥2, $R^2$'s may be identical to or different from each other.

The hydrocarbyl or heterohydrocarbyl refers to a radical having one binding site derived from hydrocarbon or heterohydrocarbon, the hydrocarbylene or heterohydrocarbylene refers to a radical having two binding sites derived from hydrocarbon or heterohydrocarbon, and the meaning of hetero is carbon being substituted by a heteroatom such as O, S, N, B, Si, and P.

In addition, a substitution is replaced with a substituent selected from the group consisting of hydrocarbyl, heterohydrocarbyl, halogen, and the like, and as a non-limiting example, the substituent is selected from the group consisting of (C6-C20)aryl, (C6-C20)ar(C1-C10)alkyl, (C1-C10)alkyl, (C2-C10)alkenyl, (C2-C10)alkynyl, (C3-C7)cycloalkyl, (C5-C20)heteroaryl, (C3-C7)heterocycloalkyl, (C1-C10)alkoxy, (C6-C20)aryloxy, —$NR^{21}R^{22}$, fluoro, chloro, bromo, iodo, and the like, $R^{21}$ and $R^{22}$ are independently of each other selected from the group consisting of hydrogen, (C1-C10)alkyl, (C1-C10)alkoxy, (C6-C20)aryl, (C6-C20)aryloxy, and the like, and naturally, alkyl, alkoxy, aryl, or aryloxy of $R^{21}$ and $R^{22}$ may be independently of each other further substituted by one or more selected from the group consisting of (C1-C10)alkyl, (C1-C10)alkoxy, (C6-C20)aryloxy, and a halogen, and the like.

B of the heteroatom ligand according to an exemplary embodiment of the present invention may be selected from the group consisting of organic linking groups including substituted or unsubstituted hydrocarbylene and substituted or unsubstituted heterocarbylene; and inorganic linking groups including a monoatomic link, and a non-limiting example thereof may be selected from the group consisting of organic linking groups such as methylene, dimethylmethylene, ethane-1,2-diyl, ethene-1,2-diyl, 1,2-propylene, propane-1,2-diyl, propane-1,3-diyl, cyclopropane-1,1-diyl, cyclopropane-1,2-diyl, butane-2,3-diyl, cyclobutane-1,2-diyl, cyclpentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 9,10-anthracene-diyl, 1,2-catecholate, 1,2-diarylhydrizine-1,2-diyl (—N(Ar)—N(Ar)—, wherein Ar is an aryl group), 1,2-dialkylhydrazine-1,2-diyl (—N(Alk)-N(Alk)-, wherein Alk is an alkyl or cycloalkyl group), 1-alkyl-2-arylhydrazine-1,2-diyl (—N(Alk)-N(Ar)—, wherein Alk is an alkyl or cycloalkyl group and Ar is an aryl group), —N(R')—$X_1$—N(R")— (wherein R' and R" are independently of each other an alkyl group, a cycloalkyl group, or an aryl group, and $X_1$ is a hydrocarbylene group), =C(R')—N(R")—, =C(R'—C(R") (R''')— (wherein =denotes a double bond, and R', R", and R''' are independently of one another hydrogen, an alkyl group, a cycloalkyl group, or an aryl group), —B(R')—, —Si(R')$_2$—, —P(R')—, and —N(R')— (wherein R' is hydrogen, a hydrocarbyl group, a heterohydrocarbyl group, or a halogen); and inorganic linking groups such as a monoatom or a two-atom linker sparer.

The transition metal according to an exemplary embodiment of the present invention may be preferably chromium. Chromium may be provided as one or more chromium precursors selected from the group consisting of chromium (III) acetyl acetonate, chromium trichloride tris-tetrahydrofuran, chromium(III) 2-ethylhexanoate, and the like, but is not limited thereto.

In addition, the heteroatom ligand according to an exemplary embodiment of the present invention has a skeleton structure of —P—C—C—P—, and as the structure neighboring a carbon atom between two phosphine atoms varies three-dimensionally, the activity and selectivity of the trimerization and tetramerization reactions may be changed depending on the purpose, a preferred example in terms of more easily controlling a space unsymmetrically may be a ligand of the following Chemical Formula B, and it is more preferred that the carbon in the skeleton structure has a (R,R) or (S.S) configuration pair as a chiral carbon, but not limited thereto.

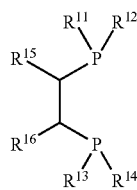

[Chemical Formula B]

wherein $R^{11}$ to $R^{14}$ are independently of one another selected from the group consisting of substituted or unsubstituted hydrocarbyl and substituted or unsubstituted heterohydrocarbyl; and $R^{15}$ and $R^{16}$ are independently of each other substituted or unsubstituted hydrocarbyl, or $R^{15}$ and $R^{16}$ may be bonded via substituted or unsubstituted hydrocarbylene or substituted or unsubstituted heterohydrocarbylene to form a ring.

In the olefin oligomerization method with reduced fouling according to an exemplary embodiment of the present invention, the main catalyst may be a compound in which chromium provided by a chromium precursor and a ligand represented by Chemical Formula B are bonded.

In the olefin oligomerization method with reduced fouling according to an exemplary embodiment of the present invention, the catalyst composition may include the cocatalyst in a range of 1 to 10000 moles, based on 1 mole of the main catalyst. Preferably, the catalyst composition may be a composition in which the main catalyst and the cocatalyst are mixed in a mole ratio of 1:10 to 1:10000, but is not limited thereto.

In the olefin oligomerization method with reduced fouling according to an exemplary embodiment of the present invention, the cocatalyst is introduced for increasing the activity of the main catalyst and implementing more stable catalytic activity, and is not limited as long as it is a commonly used compound, and a non-limiting example thereof includes organic aluminum compounds, organic boron compounds, and the like.

The organic aluminum compound may be aluminoxane, an alkylaluminum compound, an alkylaluminumchloride compound, an alkyloxyaluminum compound, an aryloxyaluminum compound, and the like.

Here, aluminoxane may have a form such as linear, cyclic, or cage, and a non-limiting example thereof may include not only alkylauminoxane selected from the group consisting of methylaluminoxane (MAO), methylisobutylaluminoxane (MMAO), ethylaluminoxane (EAO), isobutylaluminoxane (IBAO), tetraisobutylaluminoxane (TIBAO), and the like, but also modified alkylaluminoxane such as modified methylaluminoxane (mMAO) (as an example, $[(R^a)_n(R^b)_{1-n}AlO]_m$ wherein $R^a$ and $R^b$ are independently of each other hydrocarbyl, halogen-substituted hydrocarbyl, or a halogen, n is a number between 0 and 1, and m is an integer of 1 or more), and the like.

In addition, a non-limiting example of the alkylaluminum compound may include trimethylaluminum, triethylaluminum, tripropylaluminum, triisobutylaluminum, diisobutylaluminum, trioctylaluminum, and the like, and a non-limiting example of the alkylaluminumchloride compound may include dimethylaluminum chloride, diethylaluminum chloride, dipropylaluminum chloride, diisobutylaluminum chloride, dioctylaluminum chloride, methylaluminum dichloride, ethylaluminum dichloride, propylaluminum dichloride, isobutylaluminum dichloride, hexylaluminum dichloride, methylaluminum sesquichloride, ethylaluminum sesquichloride, and the like. In addition, the alkyloxyaluminum compound may be dimethylaluminum hydride, diethylaluminum hydride, dipropylaluminum hydride, diisopropylaluminum hydride, diisobutylaluminum hydride, dioctylaluminum hydride, and the like, and a non-limiting example of the aryloxyaluminum compound may include aryloxyaluminum compounds such as triphenoxyaluminum, dimethyaluminumphenoxide, and methylaluminumdiphenoxide.

In addition, a non-limiting example of the organic boron compound may be selected from the group consisting of tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl)borate, tetrakis(3,4,5-tetrafluorophenyl)borate, tetrakis(2,2,4-trifluorophenyl)borate, phenylbis(pentafluorophenyl)borate, tetrakis(3,5-bistrifluoromethylphenyl)borate, and the like; ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, triphenylmethyl tetrakis(3,5-bistrifluoromethylphenyl)borate, triethylammonium tetrakis(pentafluorophenyl)borate, tripropylammonium tetrakis(pentafluorophenyl)borate, tri(normal butyl)ammonium tetrakis(pentafluorophenyl)borate, tri(normal butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, tri(dimethylphenyl)phosphonium tetrakis(pentafluorophenyl)borate, and the like, and among them, it is preferred that the most preferred may be selected from the group consisting of N,N-dimethylanilinium tetrakispentafluorophenylborate, triphenylmethylinium tetrakispentafluorophenylborate, and trispentafluoroborane, but is not limited thereto.

Here, the cocatalyst may be included so that the mole ratio of an aluminum or boron atom is 1:0.01 to 1:1000, based on the mole ratio of the chromium atom of the main catalyst, and it is preferred that the cocatalyst is included at preferably a mole ratio of 1:0.1 to 1:500, more preferably a mole ratio of 1:0.1 to 1:100.

In the olefin oligomerization method with reduced fouling according to an exemplary embodiment of the present invention, the cocatalyst may be dissolved in a reaction solvent (medium) or may be uniformly dispersed in the reaction solvent, and a preferred example of the reaction solvent may include C3-C20 hydrocarbon-based solvents. Here, a non-limiting example of the hydrocarbon-based solvent may be one or more selected from the group consisting of butane, pentane, hexane, heptane, octane, isooctane, nonane, decane, dodecane, cyclohexane, methylcyclohexane (MCH), methylcyclopentane (MCP), benzene, toluene, xylene, ethylbenzene, and the like, and preferably one or more selected from the group consisting of cyclohexane, methylcyclohexane (MCH), methylcyclopentane (MCP), and the like, but is not limited thereto.

In the olefin oligomerization method with reduced fouling according to an exemplary embodiment of the present invention, the produced oligomer may be for example, 1-butene, 1-hexene, 1-octene, 1-decene, 1-dodecene, 1-tetradecene, 1-octadecene, and the like. In the present invention, in particular, 1-hexene and 1-octene may be prepared with high selectivity, and thus, these products are prioritized. In addition, according to the present invention, it was found that during the oligomerization reaction using an olefin, with a reduced selectivity to polyolefin which may be formed as a by-product in addition to 1-hexene and 1-octene, not only the total production amount of polyolefin may be minimized, but also the phenomenon of fouling in the inner wall of the reactor by the produced by-products may be fundamentally prevented.

Besides, the oligomerization reaction may be performed under a slurry phase condition, a solution phase, or the like, of course.

The olefin oligomerization method with reduced fouling according to an exemplary embodiment of the present invention may be performed at any appropriate temperature. Here, the appropriate temperature may be 0 to 200° C., and it is preferred that the method is performed at preferably at 40 to 100° C., and more preferably at 40 to 70° C.

In addition, the reaction solvent to be used under the solution phase condition is not limited, but may be selected from C3-C20 hydrocarbon-based solvents, and a non-limiting example of the hydrocarbon-based solvent may be one or more selected from the group consisting of butane, pentane, hexane, heptane, octane, isooctane, nonane, decane, dodecane, cyclohexane, methylcyclohexane (MCH), methylcyclopentane (MCP), benzene, toluene, xylene, ethylbenzene, and the like, and preferably one or more selected from the group consisting of hexane, heptane, cyclohexane, methylcyclohexane (MCH), methylcyclopentane (MCP), and the like.

In addition, the olefin oligomerization method with reduced fouling according to an exemplary embodiment of the present invention may be performed under an atmospheric pressure (1 bar) to 800 bar, preferably an atmospheric pressure to 100 bar, and more preferably an atmospheric pressure to 60 bar.

According to the present invention, it was confirmed that the production amount of the sticking by-products is effectively suppressed by introducing the ionic compound, and also the production amounts of floating by-products as well as the sticking by-products are dramatically suppressed by using a predetermined ionic compound, thereby fundamentally preventing fouling of the by-products produced during the reaction in the inner wall of a reactor.

In the olefin oligomerization method with reduced fouling according to an exemplary embodiment of the present invention, the olefin oligomerization catalyst composition may be a composition in which main catalyst: cocatalyst is mixed in a range of a mole ratio of 1:10 to 1:10000, but is not limited thereto.

According to an exemplary embodiment of the present invention, an α-olefin oligomer composition including an ionic compound and an α-olefin oligomer is included.

As the α-olefin oligomer according to an exemplary embodiment of the present invention, 1-hexene, 1-octene, or a mixture thereof is prioritized.

Here, the content of the ionic compound in the α-olefin oligomer composition is not limited, but the ionic compound may be contained at 0.001 to 1,000 ppm, 0.01 to 500 ppm, 0.1 to 50 ppm, or 10 to 30 ppm in the α-olefin oligomer composition.

The present invention may be understood more clearly by the following examples, and the following examples are only illustrative of the present invention and are not to limit the scope of the present invention. In addition, the following examples of the present invention were performed in a semi-batch reactor except where otherwise stated, and all of the organic solvents used in the reaction was used after passing the solvent through a tube filled with silica gel and molecular sieve 5A active alumina and bubbling it through high-purity nitrogen to sufficiently remove moisture, oxygen, other catalytic poison materials, and the like therefrom. All of the reactions was allowed to proceed under a nitrogen atmosphere, and most of the reagents were used by purchasing the products from Aldrich or STREM. Methylaluminoxane or modified aluminoxane (as an example, mMAO-12, mMAO-3A, or mMAO-7) was used by purchasing a product from AkzoNobel. The molecular weight of methylaluminoxane was calculated as 58.016 g/mol and the molecular weight of modified aluminoxane (mMAO-3A) used in the examples was calculated as 70.07 g/mol. The amounts of the reaction products obtained in the following examples and comparative examples were analyzed by the following method:

1. Contents (wt %) of 1-hexene and 1-octene in reaction product (LAO)

wt % of 1-hexene and 1-octene in the reaction solution was analyzed using Agilent GC 7890.

2. Analysis of content (wt %) of polyethylene (total PE) obtained as by-product after reaction The content of polyethylene obtained as a by-product after the reaction refers to a total content of polyethylene including a primary by-product (floating polyethylene, $1^{st}$ PE) and a secondary by-product (sticking polyethylene, $2^{nd}$ PE). The floating polyethylene is a solid separated after filtering a reaction product, and the sticking polyethylene refers to a solid attached to the inside of the reactor. Each solid was dissolved in benzene heated to 70° C. and dried in a vacuum oven at 60° C. for 8 hours, and the weight was measured, thereby analyzing each content (wt %).

Preparation Example 1

Preparation of bis-[(S,S)-(phenyl)$_2$PCH(methyl)CH(methyl)P(phenyl)$_2$chromium dichloride(μ-chloride)] ([CrCl$_2$(μ-Cl){(P,P)-k2-(S,S)-((Ph)$_2$P(Me)CH—CH (Me)P(Ph)$_2$)}]$_2$)

1.1 g(3.0 mmol) of tris-tetrahydrofuran chromium trichloride (CrCl$_3$(THF)$_3$) was dissolved in 100 mL of methane dichloride, and then 1.28 g(3.0 mmol) of a (S,S)-(phenyl)$_2$PCH(methyl)CH(methyl)P(phenyl)$_2$ ligand compound was also dissolved in 50 mL of methane dichloride and slowly added thereto. The reactant was stirred for 3 hours, a volatile matter was removed under vacuum, and 100 mL of petroleum ether was added dropwise to obtain a blue solid as a precipitate. The solid was washed twice with 100 mL of petroleum ether to obtain 1.58 g of a title compound (yield 90%).

Example 1

1 L of methylcyclohexane (MCH) was introduced to a semi-batch reactor having a volume of 2 L which was substituted with nitrogen after sufficient drying, and 20 mg of sodium chloride (NaCl) was dispersed in 10 mL of MCH and introduced to the semi-batch reactor. 1.57 g(4 mmol) of heptane solution of a cocatalyst of 18 wt % mMAO-3A was introduced to the reactor, and the temperature of the semi-batch reactor was heated to 60° C. Thereafter, the pressure in the reactor was filled with ethylene to 27 bar. 3.1 mg of bis-[(S,S)-(phenyl)$_2$PCH(methyl)CH(methyl)P(phenyl)$_2$chromium dichloride(μ-chloride)] (5.3 μmol-Cr) was introduced to an upper catalyst port of the semi-batch reactor, the pressure in the reactor was filled with ethylene to 30 bar, ethylene was continuously supplied, and an oligomerization reaction was performed for 80 minutes (stirring condition: 200 rpm). Thereafter, 100 mL of ethanol containing 10 vol % aqueous hydrochloric acid solution (wt:wt, 10 vol % hydrochloric acid:ethanol=1:1) was introduced to the reaction solution to complete the reaction, and the reaction product was filtered and separated. The reaction product recovered from the reaction filtrate was dried in a vacuum oven at 60° C. for 8 hours.

The weight of the primary by-product recovered by filtration was measured. In addition, 1 L of MCH was introduced to the semi-batch reactor from which the reaction product was removed (FIG. 1) and stirred at 150° C. for 1 hour, then the reaction solution was drained, and the weight of the secondary by-product was measured.

As a result, the reaction product (LAO, C6+C8) was obtained at a ratio of 1.36 (C8/C6), the total amount of polyethylene (total PE) obtained as a by-product was 2.61 g, and among them, the primary by-product weighed 1.83 g and the secondary by-product weighed 0.79 g (see the following Table 1).

Example 2

A reaction product was obtained in the same manner as in Example 1, except that sodium phosphate (Na$_3$PO$_4$) was used instead of sodium chloride (NaCl), and the primary by-product and the secondary by-product were weighed in the same manner as in Example 1.

As a result, the reaction product (LAO, C6+C8) was obtained at a ratio of 1.58 (C8/C6), the total amount of polyethylene (total PE) obtained as a by-product was 1.52 g, and among them, the primary by-product weighed 0.82 g and the secondary by-product weighed 0.70 g (see the following Table 1).

Example 3

A reaction product was obtained in the same manner as in Example 1, except that imidazolium chloride was used instead of sodium chloride (NaCl), and the primary by-product and the secondary by-product were weighed in the same manner as in Example 1.

As a result, the reaction product (LAO, C6+C8) was obtained at a ratio of 1.48 (C8/C6), the total amount of polyethylene (total PE) obtained as a by-product was 1.55 g, and among them, the primary by-product weighed 0.98 g and the secondary by-product weighed 0.57 g (see the following Table 1).

Example 4

A reaction product was obtained in the same manner as in Example 1, except that tetrabutylammonium cyanide (TBACN) was used instead of sodium chloride (NaCl), and the primary by-product and the secondary by-product were weighed in the same manner as in Example 1.

As a result, the reaction product (LAO, C6+C8) was obtained at a ratio of 1.91 (C8/C6), the total amount of polyethylene (total PE) obtained as a by-product was 0.64 g, and among them, the primary by-product weighed 0.29 g and the secondary by-product weighed 0.35 g (see the following Table 1).

Example 5

A reaction product was obtained in the same manner as in Example 1, except that tetrabutylammonium chloride (TBACl) was used instead of sodium chloride (NaCl), and the primary by-product and the secondary by-product were weighed in the same manner as in Example 1.

As a result, the reaction product (LAO, C6+C8) was obtained at a ratio of 1.61 (C8/C6), the total amount of polyethylene (total PE) obtained as a by-product was 0.48 g, and among them, the primary by-product weighed 0.36 g and the secondary by-product weighed 0.12 g (see the following Table 1).

Example 6

A reaction product was obtained in the same manner as in Example 1, except that sodium iodide (NaI) was used instead of sodium chloride (NaCl), and the primary by-product and the secondary by-product were weighed in the same manner as in Example 1.

As a result, the reaction product (LAO, C6+C8) was obtained at a ratio of 1.33 (C8/C6), the total amount of polyethylene (total PE) obtained as a by-product was 0.95 g, and among them, the primary by-product weighed 0.29 g and the secondary by-product weighed 0.66 g (see the following Table 1).

Example 7

A reaction product was obtained in the same manner as in Example 1, except that sodium bromide (NaBr) was used instead of sodium chloride (NaCl), and the primary by-product and the secondary by-product were weighed in the same manner as in Example 1.

As a result, the reaction product (LAO, C6+C8) was obtained at a ratio of 1.31 (C8/C6), the total amount of polyethylene (total PE) obtained as a by-product was 1.53 g, and among them, the primary by-product weighed 0.82 g and the secondary by-product weighed 0.71 g (see the following Table 1).

Example 8

A reaction product was obtained in the same manner as in Example 1, except that potassium bromide (Kbr) was used instead of sodium chloride (NaCl), and the primary by-product and the secondary by-product were weighed in the same manner as in Example 1.

As a result, the reaction product (LAO, C6+C8) was obtained at a ratio of 1.29 (C8/C6), the total amount of polyethylene (total PE) obtained as a by-product was 1.79 g, and among them, the primary by-product weighed 0.98 g and the secondary by-product weighed 0.81 g (see the following Table 1).

Comparative Example 1

A reaction product was obtained in the same manner as in Example 1 except that sodium chloride (NaCl) was not used.

Thereafter, the weight of the primary by-product recovered by filtration was measured. In addition, 1 L of MCH was introduced to the semi-batch reactor from which the reaction product was removed (FIG. 2) and stirred at 150° C. for 1 hour, then the reaction solution was drained, and the weight of the secondary by-product was measured.

Each weight measured is shown in the following Table 1.

Comparative Example 2

A reaction product was obtained in the same manner as in Example 1, except that polypropylene glycol (Sigma-Aldrich, Mw=2000, PPG 2000) was used instead of sodium chloride (NaCl), and the primary by-product and the secondary by-product were weighed in the same manner as in Example 1.

Each weight measured is shown in the following Table 1.

Comparative Example 3

A reaction product was obtained in the same manner as in Example 1, except that triethylamine (Sigma-Aldrich, TEA) was used instead of sodium chloride (NaCl), and the primary by-product and the secondary by-product were weighed in the same manner as in Example 1.

TABLE 1

| Example | Antifouling agent Type | Use amount (ppm) | Production amount of LAO (g, C6 + C8) | Total PE wt % | $2^{nd}$ PE (g) | $2^{nd}$ PE reduction (%) |
|---|---|---|---|---|---|---|
| 1 | NaCl | 20 | 532 | 0.49 | 0.79 | 30.09 |
| 2 | $Na_3PO_4$ | 20 | 570 | 0.27 | 0.7 | 38.05 |
| 3 | Imidazolium chloride | 20 | 502 | 0.31 | 0.57 | 49.56 |
| 4 | TBACN | 20 | 298 | 0.21 | 0.35 | 69.03 |
| 5 | TBACl | 20 | 372 | 0.13 | 0.12 | 89.38 |
| 6 | NaI | 20 | 528 | 0.18 | 0.66 | 41.59 |
| 7 | NaBr | 20 | 519 | 0.29 | 0.71 | 37.17 |
| 8 | KBr | 20 | 512 | 0.35 | 0.81 | 28.32 |
| Comparative Example 1 | — | — | 549 | 0.47 | 1.13 | — |
| Comparative Example 2 | PPG 2000 | 20 | 13 | 21.38 | 2.36 | −108.85 |
| Comparative Example 3 | TEA | 20 | 426 | 0.64 | 1.62 | −43.36 |

*$2^{nd}$ PE reduction (%) represents a reduction ratio relative to Comparative Example 1, and is a numerical value calculated from the following equation.
[Equation] $2^{nd}$ PE reduction (%) = 100 − {($2^{nd}$ PE production amount of Example #/$2^{nd}$ PE production amount of Comparative Example 1) × 100}

As shown in Table 1, according to the present invention, it was confirmed that not only 1-hexene and 1-octene may be produced in a high yield under mild conditions, but also the production amount of the secondary by-product which is sticking polyethylene in the polyethylene produced as a by-product (total PE) may be effectively reduced. In particular, it is preferred to use a predetermined inorganic salt including an anionic component selected from the group consisting of halide groups and phosphate groups as the antifouling agent, since the production amount of the secondary by-product may be dramatically reduced.

Moreover, it was confirmed that when the predetermined ionic compound is used, not only the production amount of the secondary by-product, but also the production amount of the primary by-product which is floating polyethylene is reduced simultaneously, thereby effectively suppressing a fouling phenomenon which may occur in the reaction. In particular, it is preferred to use an organic salt including a predetermined ionic compound including a cationic component selected from the group consisting of tetraalkylammonium and tetraalkylphosphonium, since the production amount of total PE as well as the production amount of the secondary by-product may be dramatically reduced.

The effect as such has not been recognized in the conventional art, and there was no specific application example therefor.

As described above, though the exemplary embodiments of the present invention have been described in detail, a person skilled in the art may make various variations of the present invention without departing from the spirit and the scope of the present invention, as defined in the claims which follow. Accordingly, future modification of the examples of the present invention is also included in the protection scope of the present invention.

The invention claimed is:

1. An olefin oligomerization method, comprising:
   introducing an antifouling agent including an inorganic compound to a medium into a reactor;
   introducing a catalyst composition to the reactor; and
   introducing an olefin to the reactor to subject the olefin to an oligomerization reaction.

2. The olefin oligomerization method of claim 1, wherein the inorganic compound is an inorganic salt including a metal ion selected from the group consisting of alkali metals, alkali earth metals, transition metals, post-transition metals, and metalloids.

3. The olefin oligomerization method of claim 2, wherein the inorganic compound is an alkali metal salt.

4. The olefin oligomerization method of claim 1, wherein in the step of introducing the antifouling agent, introducing an organic salt containing a cation selected from the group consisting of ammonium, phosphonium, pyridinium, imidazolium, imidazolinium, pyrazolium, sulfonium, pyrrolidinium, and piperidinium.

5. The olefin oligomerization method of claim 4, wherein the organic salt is a tetraalkylammonium salt or a tetraalkylphosphonium salt.

6. The olefin oligomerization method of claim 5, further comprising an organic salt selected from the group consisting of tetraalkylammonium phosphate-based compounds, tetraalkylammonium sulfate-based compounds, tetraalkylammonium halide-based compounds, tetraalkylammonium pseudohalide-based compounds, tetraalkylphosphonium phosphate-based compounds, tetraalkylphosphonium sulfate-based compounds, tetraalkylphosphonium halide-based compounds, and tetraalkylphosphonium pseudohalide-based compounds.

7. The olefin oligomerization method of claim 1, wherein the inorganic compound includes a halide group.

8. The olefin oligomerization method of claim 1, wherein the inorganic compound is included at 0.001 to 1,000 ppm, based on a total weight of a medium in the reactor.

9. The olefin oligomerization method of claim 1, wherein the catalyst composition includes a main catalyst and a cocatalyst, and the main catalyst is a complex in which a transition metal and a heteroatom ligand represented by the following Chemical Formula A are coordinately bonded:

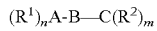   [Chemical Formula A]

wherein

A and C are independently of each other selected from the group consisting of phosphorus, arsenic, antimony, oxygen, bismuth, sulfur, selenium, and nitrogen, B is a linking group between A and C, n and m are independently of each other an integer determined by each of valency and oxidation state of A or C, and $R^1$ and $R^2$ are independently of each other selected from the group consisting of substituted or unsubstituted hydrocarbyl and substituted or unsubstituted heterohydrocarbyl, and when n≥2, $R^1$'s may be identical to or different from each other, and when m≥2, $R^2$'s may be identical to or different from each other.

10. The olefin oligomerization method of claim 1, wherein the oligomerization reaction is performed at a temperature in a range of 0 to 200° C.

11. The olefin oligomerization method of claim 1, wherein the oligomerization reaction is performed at a temperature in a range of 40 to 100° C.

12. The olefin oligomerization method of claim 1, wherein the oligomerization reaction is performed under a pressure in a range of 1 to 800 bar.

13. The olefin oligomerization method of claim 1, wherein 1-hexene, 1-octene, or a mixture thereof is selectively prepared.

* * * * *